(12) United States Patent
Alkusayer

(10) Patent No.: US 9,663,381 B2
(45) Date of Patent: May 30, 2017

(54) AMMONIA SYNTHESIS FOR FERTILIZER PRODUCTION

(71) Applicant: RITAJ INV., Al Riyadh (SA)

(72) Inventor: Khalid T. Alkusayer, Almorooj Riyadh (SA)

(73) Assignee: RITAJ, INV., Al Riyadh (SA)

( * ) Notice: Subject to any disclaimer, the term of this patent is extended or adjusted under 35 U.S.C. 154(b) by 0 days.

(21) Appl. No.: 15/093,998

(22) Filed: Apr. 8, 2016

(65) Prior Publication Data

US 2016/0251229 A1    Sep. 1, 2016

Related U.S. Application Data

(63) Continuation of application No. 14/992,204, filed on Jan. 11, 2016.
(Continued)

(51) Int. Cl.
*C01C 1/04* (2006.01)
*B01J 19/24* (2006.01)
(Continued)

(52) U.S. Cl.
CPC ......... *C01C 1/0488* (2013.01); *B01J 19/0006* (2013.01); *B01J 19/24* (2013.01);
(Continued)

(58) Field of Classification Search
CPC .................................................... C01C 1/04
See application file for complete search history.

(56) References Cited

U.S. PATENT DOCUMENTS 4,197,281 A    4/1980   Muenger et al.
4,762,535 A *  8/1988   Pez ........................ B01D 61/38
                                                          95/44
(Continued)

OTHER PUBLICATIONS

Catalano, Jacopo, Federico Guazzone, Ivan P. Mardilovich, Nikolaos K. Kzantzis, and Yi Hua Ma. Hydrogen Production in a Large Scale Water-Gas Shift Pd-Based Catalytic Membrane Reactor. Worcester Polytechnic Institute, Dec. 21, 2011. Web. Apr. 2, 2015. <http://pubs.acs.org/doi/abs/10.1021/ie2025008>, pp. 1-15.

(Continued)

*Primary Examiner* — Wayne Langel
(74) *Attorney, Agent, or Firm* — Chapin Intellectual Property Law, LLC

(57) ABSTRACT

A method for synthesizing ammonia for agricultural fertilizers employs water (H2O) as the source of hydrogen (H2) in ammonia (NH3) synthesis, and gathers carbon monoxide (CO) as a limiting reagent for combining in a WGS (Water-Gas-Shift) reaction for producing hydrogen. The WGS reaction employs CO with the water to produce Carbon Dioxide (CO2) and H2, consuming undesirable CO from other industrial applications. A by-product of the process includes generating 1.5 mole of CO2 for each mole of ammonia synthesized. An intermediate step consumes 3 moles of hydrogen for each mole of Nitrogen (N2). The use of methane gas is avoided as the process employs CO and the WGS reaction as an exclusive source of H2 without introducing methane (CH4). A downstream synthesis of ammonia can be done through a fuel cell to produce electricity for the ammonia synthesis for further sustainability.

9 Claims, 7 Drawing Sheets

Related U.S. Application Data

(60) Provisional application No. 62/121,039, filed on Feb. 26, 2015.

(51) Int. Cl.

| | | |
|---|---|---|
| *C01B 3/06* | (2006.01) | |
| *C01B 3/58* | (2006.01) | |
| *C07C 273/10* | (2006.01) | |
| *B01J 19/00* | (2006.01) | |
| *C01B 3/02* | (2006.01) | |
| *C01B 3/16* | (2006.01) | |
| *C01B 3/50* | (2006.01) | |

(52) U.S. Cl.
CPC ............ *B01J 19/2475* (2013.01); *C01B 3/025* (2013.01); *C01B 3/06* (2013.01); *C01B 3/16* (2013.01); *C01B 3/505* (2013.01); *C01B 3/58* (2013.01); *C01C 1/0405* (2013.01); *C01C 1/0411* (2013.01); *C01C 1/0417* (2013.01); *C01C 1/0452* (2013.01); *C01C 1/0458* (2013.01); *C07C 273/10* (2013.01); *B01J 2219/00058* (2013.01); *B01J 2219/24* (2013.01); *C01B 2203/0283* (2013.01); *C01B 2203/041* (2013.01); *C01B 2203/0435* (2013.01); *C01B 2203/066* (2013.01); *C01B 2203/068* (2013.01); *C01B 2203/1205* (2013.01)

(56) References Cited

U.S. PATENT DOCUMENTS

| | | | |
|---|---|---|---|
| 6,448,441 B1 | 9/2002 | Wing-Chiu et al. | |
| 7,300,642 B1 | 11/2007 | Pedersen et al. | |
| 7,435,401 B2* | 10/2008 | Barnett | B01J 8/067 422/148 |
| 7,641,881 B2* | 1/2010 | Steinberg | C01B 3/342 252/375 |
| 7,892,511 B2* | 2/2011 | Strait | C01B 3/586 423/360 |
| 8,685,358 B2* | 4/2014 | Allam | C01B 3/025 423/359 |
| 8,871,063 B2* | 10/2014 | Panza | B01D 53/323 204/157.3 |
| 9,005,422 B2 | 4/2015 | Jiang et al. | |
| 9,085,512 B2 | 7/2015 | Collins et al. | |
| 9,139,431 B2* | 9/2015 | Panza | C01B 3/025 |
| 2010/0044642 A1 | 2/2010 | Dijkstra et al. | |
| 2014/0120023 A1* | 5/2014 | Singh | B01J 14/00 423/359 |
| 2014/0364647 A1* | 12/2014 | Iaquaniello | C01B 3/025 564/69 |
| 2015/0125377 A1 | 5/2015 | Himstedt et al. | |
| 2015/0291438 A1* | 10/2015 | Merritt | C01C 1/0488 423/352 |

OTHER PUBLICATIONS

United States. Environmental Protection Agency. Technical Support Division. Background Report AP-42 Section 5.2: Synthetic Ammonia. Research Triangle Park, NC, pp. 1-37.

Incitec Pivot Limted. Louisiana Ammonia Plant. Dyno Nobel, Apr. 17, 2013. Web. Aug. 4, 2015. <http://www.asx.com.au/asxpdf/20130417/pdf/42f9brx9b4xscx.pdf>. pp. 1-18.

Vorotto, Alesandro, PhD. "Raising the Standards: Enhanced Catalytic Performance for Global Ammonia Production." Quantumsphere. Web. May 31, 2015. <http://qsinano.com/wp-content/uploads/2014/08/QSI-Ammonia-Whitepaper-FINAL-12-Aug-14.pdf>. pp. 1-13.

Ma, Liang-Chih, Bernardo Castro-Dominguez, Nikolaos K. Kazantzis, and Yi Hua Ma. Integration of Membrane Technology into Hydrogen Production Plants With CO2 Capture: An Economic Performance Assessment Study. Tech. Worcester, MA: Worcester Polytechnic Institute, 2015. pp. 1-15.

International Search Report and Written Opinion, PCT/IB2016/050588, pp. 6.

\* cited by examiner

| Reference Number | Stream Description | Contents | Temp (°C) | Pressure (psi) | Mass Flow Rate (kg/hr) |
|---|---|---|---|---|---|
| 1 | Gas feed to Scrubber | $CO$, $SO_2$, $HS_2$, other | 25 | 20 | 116,600 |
| 2 | Water feed to Scrubber | $H_2O$ | 25 | 20 | 958,000 |
| 3 | CO exit from Scrubber | $CO$ | 25 | 17 | 105,105 |
| 4 | Sulfur Recovery input | $H_2O$, $SO_2$, $H_2S$, other | 25 | 17 | 966,495 |
| 5 | Water feed to Heater | $H_2O$ | 25 | 20 | 139,000 |
| 6 | Heated water feed to Mixer 1 | $H_2O$ | 127 | 17 | 139,000 |
| 7 | Mixer exit | $CO$, $H_2O$ | 110 | 15 | 247,100 |
| 8 | Pre-WGS Compressor exit | $CO$, $H_2O$ | 700 | 780 | 247,100 |
| 9 | Pre-WGS Cooler exit | $CO$, $H_2O$ | 400 | 777 | 247,100 |
| 10 | Hydrogen produced from WGS | $H_2$ | 400 | 20 | 7,355 |
| 11 | WGS Purge | $CO$, $H_2O$ | 400 | 730 | 239,745 |
| 12 | Air input to $N_2$ Compressor | Air | 25 | 14.7 | 275,500 |
| 13 | Air input to Air Cooler | Air | 380 | 240 | 275,500 |
| 14 | Air input to $N_2$ Membrane | Air | 50 | 237 | 275,500 |
| 15 | Air exit from $N_2$ Membrane | Air | 50 | 235 | 223,960 |
| 16 | Nitrogen feed to Mixer 2 | $N_2$ | 50 | 20 | 51,485 |
| 17 | Feed to $1^{st}$ stage Compressor | $H_2$, $N_2$ | 170 | 18 | 58,840 |
| 18 | Feed to intermediate Cooler | $H_2$, $N_2$ | 650 | 295 | 58,840 |
| 19 | Feed to $2^{nd}$ stage Compressor | $H_2$, $N_2$ | 185 | 290 | 58,840 |
| 20 | Feed to Mixer 3 | $H_2$, $N_2$ | 600 | 2955 | 58,840 |
| 21 | Feed to Ammonia Reactor | $H_2$, $N_2$ | 450 | 2950 | 294,200 |
| 22 | Ammonia Reactor outlet | $H_2$, $N_2$, $NH_3$ | 480 | 2650 | 294,200 |
| 23 | Ammonia Product | $NH_3$ | 100 | 2645 | 58,800 |
| 24 | Recycle kettle gas outlet | $H_2$, $N_2$ | 100 | 2645 | 235,360 |
| 25 | Recycle Compressor outlet | $H_2$, $N_2$ | 115 | 2960 | 235,360 |
| 26 | Recycle Heater outlet | $H_2$, $N_2$ | 415 | 2955 | 235,360 |
| 27 | Purge | | 450 | 2640 | 40 |

Fig. 3A

AMMONIA SYNTHESIS FOR FERTILIZER PRODUCTION

RELATED APPLICATIONS

This application is a continuation under 35 U.S.C. §120 of U.S. patent application Ser. No. 14/992,204, filed Jan. 11, 2016, entitled "AMMONIA SYNTHESIS FOR FERTILIZER PRODUCTION," which claims the benefit under 35 U.S.C. §119(e) of U.S. Provisional Patent Application No. 62/121,039, filed on Feb. 26, 2015, entitled "AMMONIA SYNTHESIS FOR FERTILIZER PRODUCTION," incorporated herein by reference in entirety.

BACKGROUND

The development of mass produced fertilizer revolutionized the industrial agriculture industry by maximizing the crop yield that can be grown on a given parcel of land. Fertilizers, along with irrigation systems to relieve dependence on natural precipitation, allow a predictable, optimal yield of agricultural stock from farmland. Fertilizer production employs substantial amounts of ammonia. In solid or liquid states, ammonia salts and solutions are the active components of most synthetic fertilizers used in agriculture, which consume 83% of the world's ammonia and warrant higher demands for ammonia production. The primary industrial method for ammonia synthesis is the Haber-Bosch process, created by Fritz Haber in 1905 and developed for industry by Carl Bosch in 1910. The overall process synthesizes ammonia from molecular nitrogen and hydrogen by feeding the reactants over iron catalysts at a high pressure and temperature, requiring bulky, well-insulated reactors to house the process, and large quantities of natural gas.

The Haber process synthesizes approximately 150 million tons of ammonia each year and has allowed the earth to sustain a greatly increased population. However, the use of natural gas as a source of hydrogen and energy needed to derive nitrogen from atmospheric air have been the subjects of environmental concern. The industrial use and geological extraction of natural gas are known to contribute to carbon dioxide emissions and water pollution, respectively, and today an estimated 59% of natural gas produced in the United States is used in ammonia synthesis to meet the high demand of gaseous hydrogen. Approximately 80% of ammonia synthesized today is eventually converted into urea fertilizer, a dense nitrate that is more stable at room temperature, allowing easier storage and transportation than ammonia.

SUMMARY

A method for synthesizing ammonia for agricultural fertilizers employs water ($H_2O$) as the source of hydrogen ($H_2$) in ammonia ($NH_3$) synthesis, and gathers carbon monoxide (CO) as a limiting reagent for combining in a WGS (Water-Gas-Shift) reaction for producing hydrogen. The WGS reaction employs CO with the water to produce Carbon Dioxide ($CO_2$) and $H_2$, consuming undesirable CO from other industrial applications. A by-product of the process includes generating 1.5 mole of $CO_2$ for each mole of ammonia synthesized. An intermediate step consumes 3 moles of hydrogen for each mole of Nitrogen (N2). The use of methane gas is avoided as the process employs CO and the WGS reaction as an exclusive source of $H_2$ without introducing methane ($CH_4$). Methane production is expensive and burdens the conventional approaches.

Configurations herein are based, in part, on the observation that conventional approaches to ammonia synthesis for urea and fertilizer production employ a water-gas shift (WGS) with hydrogen $H_2$ and carbon monoxide (CO). Unfortunately, conventional approaches suffer from the shortcoming that they tend to rely heavily on natural gas such as methane as a source of hydrogen, resulting in a substantial discharge of $CO_2$ as a byproduct. Accordingly, configurations herein substantially overcome the above-described shortcomings by employing only water as the hydrogen source for ammonia synthesis. The disclosed process employs the WGS reaction as the hydrogen producing step, and entails the use of carbon monoxide for producing the raw materials needed for hydrogen production as $(CO+H_2O) \rightarrow (CO_2+H_2)$. The limiting reagent in this process is therefore the CO. Different sources can be used for CO input such as carbon black manufacturing, steel mills, electrical generation plants, or other industrial processes.

In conventional approaches, the processes by which ammonia and urea are synthesized can be summarized as simplified stoichiometric equations:

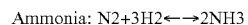
Ammonia: N2+3H2⇌2NH3

Then in another industrial location or plant:

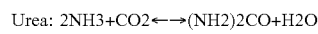
Urea: 2NH3+CO2⇌(NH2)2CO+H2O

Or 2NH3 +½O2+CO⇌(NH2)2CO+H2O

Urea is significant because 80% of the ammonia manufactured today becomes feedstock for the manufacture of urea, a more stable nitrate used for fertilizer. However, the modern syntheses of ammonia and urea require several necessary and costly processes and treatments to achieve the highest yield possible, which must be considered to accurately assess their effectiveness, as well as their impacts on the environment and industry.

In further detail, the disclosed method for synthesizing ammonia includes receiving carbon monoxide (CO) from an industrial process, and providing the received carbon monoxide to a hydrogen separator for reacting the carbon monoxide with water from a water source for producing hydrogen ($H_2$). A mixer or other vessel combines the hydrogen with nitrogen from a nitrogen reactor for synthesizing ammonia, such that the hydrogen is generated exclusively from the water provided to the hydrogen separator, which avoids consumption of methane or other natural gas in the ammonia production process.

The disclosed method may entail a system for synthesizing ammonia from byproducts of industrial operations, including a scrubber and/or membrane separator and/or ammine absorption for receiving exhaust flue gas, in which the exhaust includes carbon monoxide, and removes sulfur based compounds from the exhaust. A CO mixer combines the scrubbed carbon monoxide with water. A hydrogen separator has a membrane for separating and passing purified hydrogen ($H_2$), and a hydrogen mixer combines the separated hydrogen with nitrogen. Finally, an ammonia reactor receives the hydrogen and nitrogen, and combines the hydrogen and nitrogen under applied heat and pressure for synthesizing ammonia, in which the hydrogen is sourced exclusively from the water passed through the hydrogen separator membrane and any residual hydrocarbons from the exhaust flue gas, in contrast to conventional methane.

The system may be further enhanced by considering the downstream synthesis of urea using a PBI phosphoric acid fuel cell that uses ammonia and purified carbon monoxide as anode fuel and oxygen from air in the cathode; this fuel cell is to produce urea, electricity and water. It was suggested to use a PAFC at about 180° C. and 30 bar. Under these conditions, it was predicted that the fuel cell will have more than 95% single pass yield, and an affiliated overall efficacy of 70% by recycling raised steam through turbines. This employs the single stage synthesis of urea illustrated in the second urea synthesis method above. The raised electricity from the fuel cell urea synthesis and water production will contribute to supplying electricity to the ammonia synthesis process making it even more sustainable and less reliant on fossil fuels.

It is suggested that through this design with an optimal CO and water input it is possible to have a urea manufacturing facility that only uses CO from flue gas, water and nitrogen and oxygen from air to synthesize urea without the need for external electricity or steam or any other raw materials. It is also suggested to use other renewable sources of electricity such as solar panels and wind mills to supply the access need of electricity without external supply.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIG. 3a correlates pressure and temperatures of a production stream depicted in FIG. 3;

DETAILED DESCRIPTION

Figure 1:
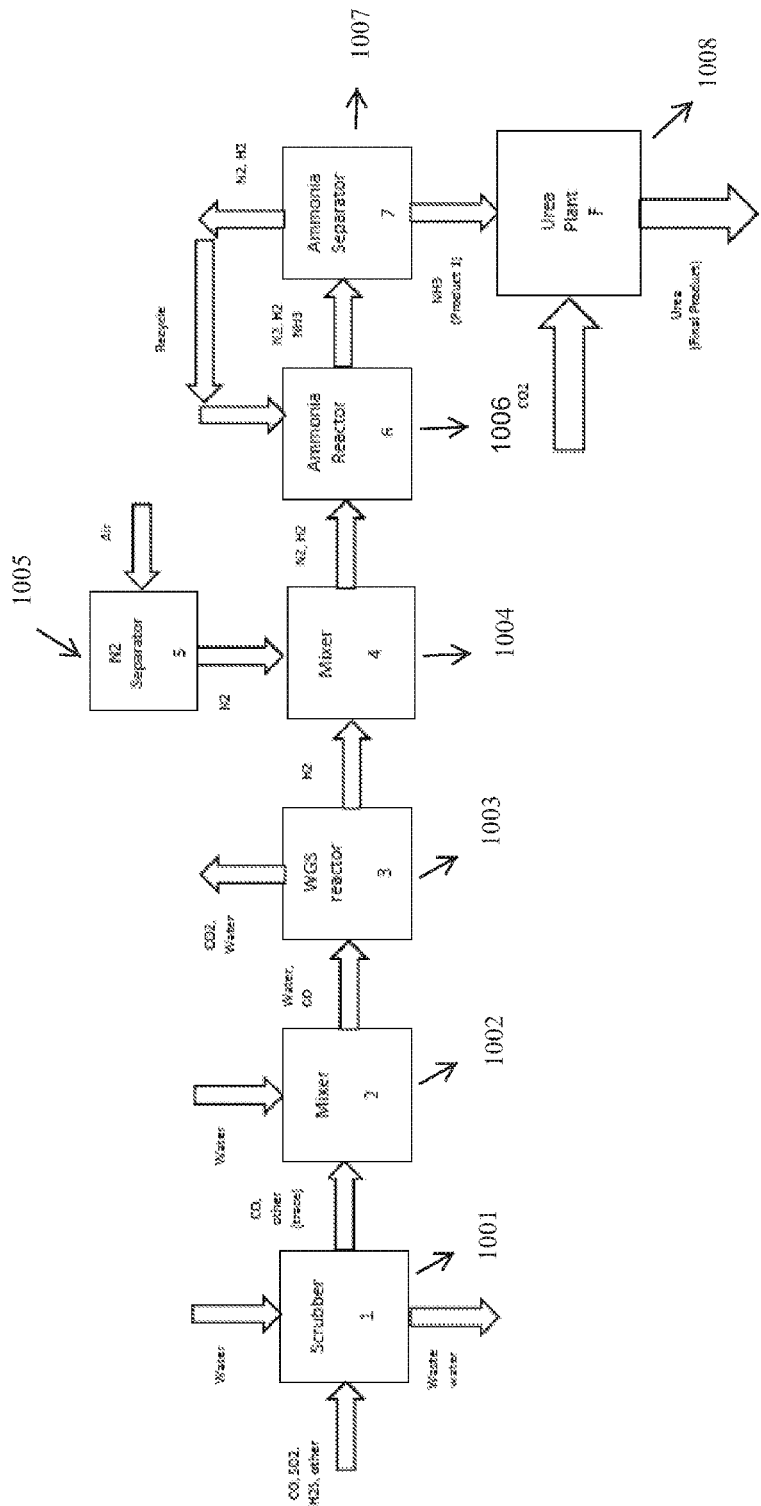
FIG. 1 is a diagram of an ammonia synthesis sequence as described herein.

Ammonia synthesis for fertilizer production has a significant environmental and atmospheric effect. The majority of greenhouse gases emitted as a result of ammonia synthesis are released through the preparation of hydrogen from the feedstock. A dramatic example would be the ammonia manufacturing plants in China, 80% of which use coal as feedstock as opposed to natural gas or naptha. Hydrogen is produced from coal through gasification (or partial oxidation), in which the coal is reacted with oxygen and steam at high temperatures and pressures. The reaction produces a synthesis gas containing hydrogen and carbon monoxide, the latter of which is reacted with excess hydrogen to form carbon dioxide which can then be removed. While plants that use coal as feedstock make up the minority of plants worldwide, China currently produces more ammonia than any other country in the world. Of the 70 million tons of ammonia produced in China annually, an estimated 80% is synthesized with hydrogen from coal—this accounts for a sizable fraction of the world's total ammonia production.

For most plants worldwide, natural gas is much more affordable than coal or heavy oil as a feedstock, and natural gas is considered to be the most sustainable of these fuels. However, the use of a cleaner feedstock does not render manufacturers unable to release the same potentially harmful compounds. In processes using the catalytic steam forming of natural gas (the vast majority of existing plants), carbon monoxide formed from the catalytic steam reforming step is reacted with excess hydrogen to form carbon monoxide, which is more easily removed from the system, similar to the process used for coal gasification. Through scrubbing, any residual carbon dioxide can be heated and purged from the system, occasionally through vents releasing it into the atmosphere. Plants have designed methods of capturing the carbon dioxide produced through steam forming, preventing the gas from entering the atmosphere and potentially repurposing the compound by feeding it into another process in which carbon dioxide is a reactant. Considering the majority of ammonia is converted to urea before it is used in fertilizers, it seems practical for carbon dioxide to be captured from steam forming and used as a reactant in urea synthesis. However, many smaller ammonia plants and plants that operate independently of urea production simply vent these fumes to the atmosphere, and even plants that recycle carbon dioxide emissions in the synthesis process where the gas is not as easily captured. The Intergovernmental Panel on Climate Change (IPCC) notes that the only plants that do not release carbon dioxide during the synthesis process are those that use a pure hydrogen feedstock rather than natural gas, which makes up a very marginal percentage of plants.

Various configurations depicting the above features and benefits as disclosed herein are shown and described further below. Mitigation of the environmental effects of ammonia and urea synthesis are depicted in an example apparatus shown and disclosed below. Alternate approaches to embody the disclosed principles.

Conventional approaches for ammonia and urea synthesis employ the well-known Haber process. This conventional approach uses methane gas ($CH_4$) and water ($2H_2O$) as the sources of hydrogen, giving off ($CO_2$, $4H_2$). However, methane can be expensive and limiting to the process. It also produces one mole of $CO_2$ as a result of the production of one mole of ammonia ($NH_3$). Configurations herein employ only water ($H_2O$) for the ammonia synthesis. This process will invoke the WGS reaction as the hydrogen producing step. This process will require the use of carbon monoxide making the raw materials needed $(CO+H_2O) \rightarrow (CO_2+H_2)$. The limiting reagent in this process will be the CO. Rather than consuming natural gas for a source of hydrogen, existing industrial sources can be used for CO input such as steel mills, different electricity generators . . . etc. The proposed ammonia synthesis process when compared to current processes used doesn't by itself generate any carbon oxides. However, for every two moles of ammonia synthesizes three moles of carbon monoxide is converted to a safer carbon oxide (carbon dioxide).

In an example configuration disclosed herein, it is proposed to have a high $CO_2$ concentration to favor the first reaction not raising pressure excessively high. The overall combined factors in an industrial setting as described above result in a lower energy profile for the proposed overall reaction:

$$3H_2O+3CO+N_2 \rightarrow (NH_2)_2CO+H_2O+2CO_2$$

RXN1: $3H_2O+3CO \rightarrow 3H_2+3CO_2$

RXN2: $N_2+3H_2 \rightarrow 2NH_3$

RXN3: $2NH_3+3CO_2 \rightarrow (NH_2)_2CO+H_2O+2CO_2$

A further advantage over conventional approaches used for the synthesis of both ammonia and urea is the thermal coupling of the two reactions. In conventional approaches, almost 60% of the ammonia produced internationally is converted to Urea. Configurations herein propose to have both ammonia and urea synthesis in one factory as a thermocoupled process, or reaction. Taking note that the WGS reaction, ammonia reaction, and urea reaction are effectively exothermic reactions, it would be beneficial to recover and redirect excess energy. Where the use of a fuel cell for the production of urea is suggested. A PAFC in a PBI arrangement is used at a temperature around 170° C. and pressure of 45 bar is initially suggested to give an overall process efficacy of 70%. Operating conditions such as minor temperature variation (160-200° C.) and pressure of (45-200 bar) and necessary resonance time of the reduction of the ammonia $R.NH_3$ to $R.NH_2$ effectively with minor losses of ammonia to $N_2$ (lower than 5%). At that temperature, the water generated at the cathode side is at a useful temperature (160-200° C.) where it goes through turbines to generate and recycle the most amount of energy. The ammonia fed to the anode is premixed with carbon monoxide at a 2:1 ratio.

FIG. 1 is a diagram of an ammonia synthesis sequence as described herein. Referring to FIG. 1. Referring to FIG. 1, the major components in the disclosed ammonia synthesis process include a scrubber and/or membrane separator and or amine absorption 1001 for receiving industrial waste gases (i.e. exhaust) and producing pure CO for use in ammonia synthesis. A mixer 1002 combines heated water with the CO, and passes it to a WGS reactor 1003. The WGS reactor 1003 separates pure hydrogen $H_2$ and emits only $CO_2$ and water as byproducts. Hydrogen generation may be augmented as discussed further below. The purified hydrogen is passed to a second mixer 1004 for receiving nitrogen $N_2$ from a nitrogen separator/generator 1005. Purified nitrogen is ideally extracted from surrounding ambient sources. An ammonia reactor 1006 receives the hydrogen and nitrogen for generating ammonia $NH_3$, and an ammonia separator 1007 separates the synthesized ammonia and recirculates the gases for resulting in a substantial ammonia yield of about 98%. The purified ammonia can then be passed to a urea plant 1008 for urea production as used in fertilizer manufacturing or other industrial uses.

Figure 2:
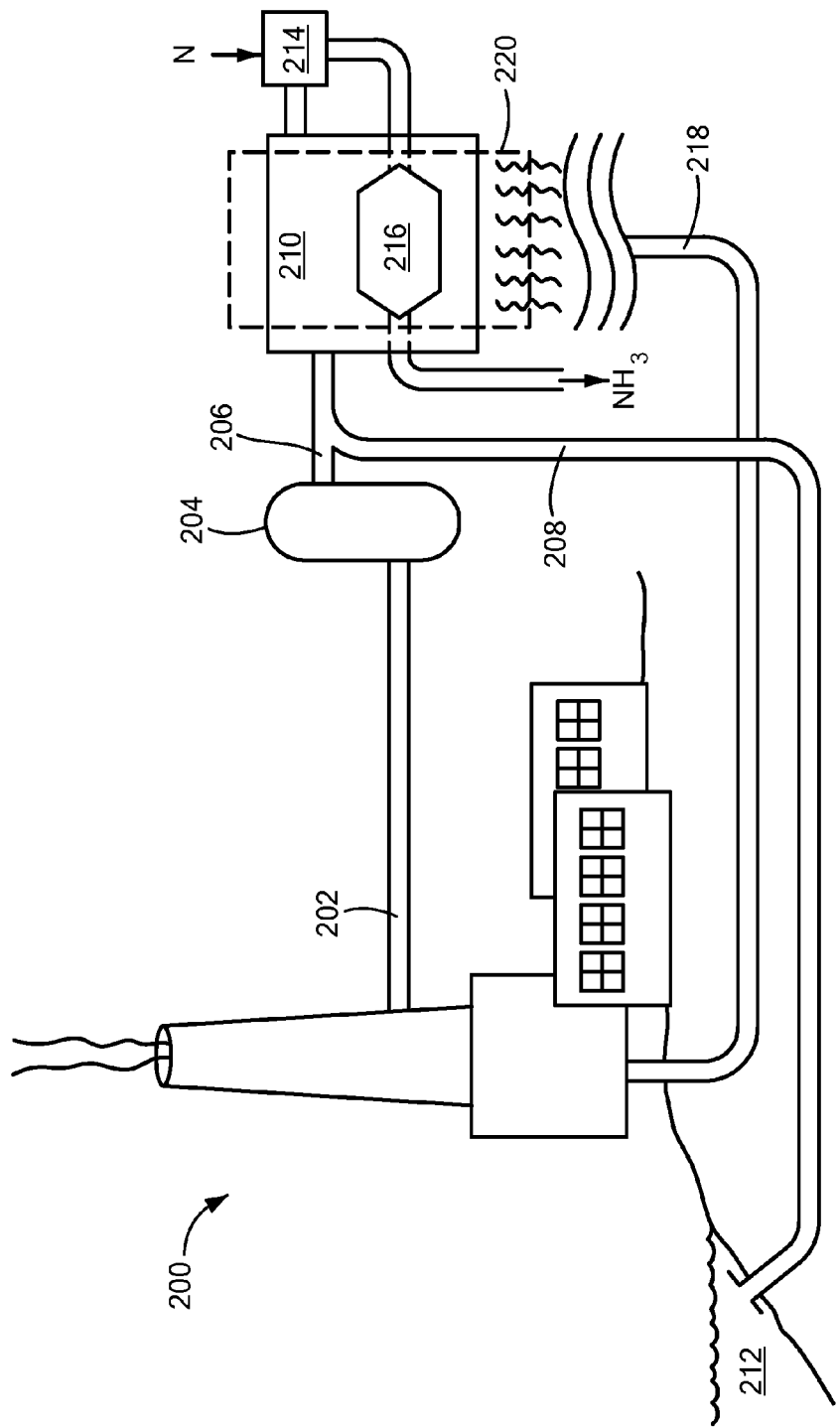
FIG. 2 shows a context diagram of an industrial environment suitable for use with configurations depicting FIG. 1.

FIG. 2 shows a context diagram of an industrial environment suitable for use with configurations depicting FIG. 1. FIG. 2 depicts one example of an industrial environment for performing the processes of FIG. 1 which attempts to arrange the steps of the ammonia synthesis in a complementary manner. Configurations herein propose an efficient ammonia and urea synthesis operation adapted to be implemented in an industrial setting where waste, byproducts, and thermal energy given off or resulting from one industrial process are received and utilized in another, to achieve as self-sustaining an operation as possible. For example, methane is an expensive hydrogen source, and imposes substantial environmental impact, so configurations herein employ CO from existing industrial combustion and water from a wastewater or industrial source to generate hydrogen gas and a byproduct of carbon dioxide ($CO_2$).

Referring to FIG. 2, a CO source 200 such as a factory or electrical plant emits exhaust including CO. The exhaust supply 202 is received by a scrubber and/or membrane and/or amine absorber 204 for separating CO from sulfides and other exhaust components. The purified CO 206 is combined with a water supply 208 in a hydrogen separator 210. The water may be sourced from any suitable source, such as a waste product of another industrial cooling operation or pumped from a nearby repository 212. A nitrogen separator 214 or nitrogen membrane provides nitrogen from ambient air sources, and combines the $N_2$ with the $H_2$ from the hydrogen separator 210 in an ammonia reactor 216. In contrast to conventional approaches, which inject substantial heat into the ammonia reactor 216, the ammonia reactor 216 may be disposed within and/or coupled thermally to the hydrogen separator 210 for mitigating heat requirements and/or may receive excess thermal energy 218 from the CO source 200. The thermal coupling 220, while not required, further reduces combustion required for ammonia production by utilizing byproducts from the CO source. In an example configuration, the CO source 200 may be a carbon black manufacturing facility, discussed further below. Thermocoupling of related processes may also occur between the heated combination of CO and $H_2O$ (206, 208) and the heating of input to the hydrogen separator 210.

Figure 3:
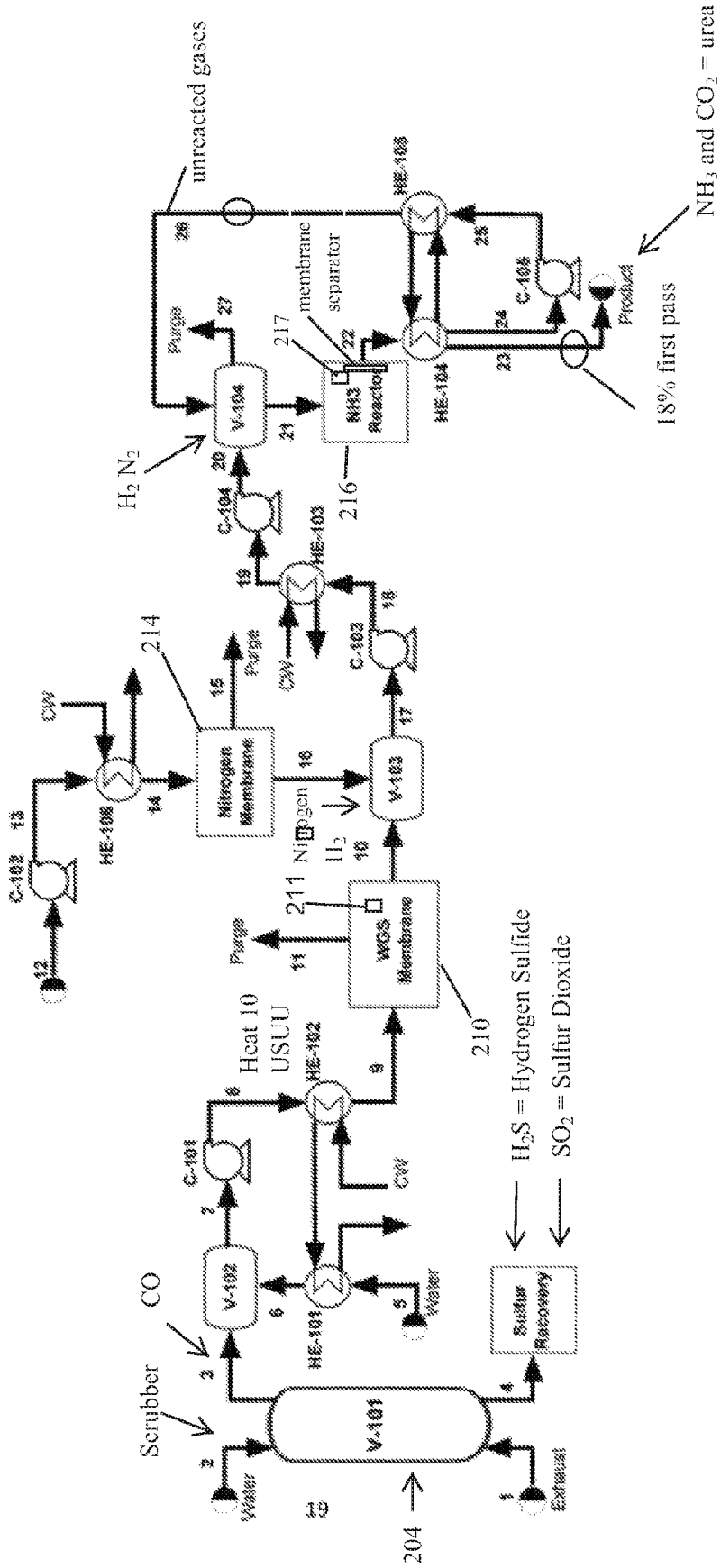
FIG. 3 shows a process flow of an ammonia and urea synthesis process of FIG. 1 in the environment of FIG. 2.

FIG. 3 shows a process flow of an ammonia and urea synthesis process of FIG. 1 in the environment of FIG. 2. FIG. 3a correlates pressure and temperatures of a production stream depicted in FIG. 3. Referring to FIGS. 2, 3 and 3a, an example plant design uses a total of five compressors, six heat exchangers, four vessels, a hydrogen separator 210 such as a water-gas shift (WGS) membrane, a nitrogen separator 214 or membrane, and an ammonia reactor 216. FIG. 3a lists the approximate or example physical properties of the referenced elements 1-27 for the example configuration. Initially, exhaust gas 1 from a carbon black refinery or manufacturing plant enters the scrubber 204 at a temperature and pressure of 25° C. and 1 ATM where the gas components are mixed with water 2 and the useful CO is separated from contaminants 4, including sulfur dioxide ($SO_2$) and hydrogen sulfide ($H_2S$). Sulfur recovery may be performed using lime, precipitating the contaminant sulfur. Lime is a very inexpensive compound, and the resulting solid can be repurposed as a filler in cement production plants, for example.

Exiting the scrubber and membrane 204, the waste water stream of sulfides in water can be saved and used for sulfur recovery. A product stream 3 containing CO is mixed in a vessel V-102 with fresh water 6 at a 2:1 molar ratio of water to CO. The water 5 is heated by heat exchanger HE-101 to combine with the CO, and is then heated to 450° C. by heat exchanger HE-102 and pressurized 8 by compressor C-101 in preparation for hydrogen separation such as from the water-gas shift reaction. Thermal coupling between HE-102 and HE-101 heating the feed water 6 may result from a common source.

For the WGS reaction in the hydrogen separator 210, the heated stream of water and CO 9 enters the hydrogen separator 210, such as an iron-chromium catalyzed membrane 211 reactor. The hydrogen separator 210 employs palladium plating to improve and promote proton transfer such that the separation reaction RXN1 (above) is undergone and pure hydrogen 10 is separated and recovered while water and $CO_2$ in a 1:1 molar ratio define a purge stream 11 for venting $CO_2$ from the production stream. With the $H_2$ feedstock secured, a nitrogen membrane separator 214 is used to isolate high-purity molecular $N_2$ 16 from the ambient air 12. Nitrogen 14 is introduced by any suitable method, such as compressing the air 13 at compressor C-102 and heating by heat exchanger HE-106.

$H_2$ gas is mixed with $N_2$ at a 3:1 molar ratio in vessel V-103, and the stream 17 pressurized 18 by compressor V-103, heated by heat exchanger HE-103 19 and pressurized to 450° C. and 200 bar 20 by compressor C-104, respectively, preparing the stream 20 for the ammonia synthesis reaction 21. An ammonia reactor 216, operating at a high temperature and pressure and equipped with an iron-chromium catalyst 217, reacts the $H_2$ and $N_2$ 22 and achieves a single-pass ammonia yield 23 of approximately 20-28%, though the product ammonia 23 is isolated using a membrane separator and heat exchanger HE-104 and the unreacted gases 24 are fed 25 by compressor C-105 back into 26 the reactor 216 until a total yield of approximately 98% of the reactant gases have been reacted.

In the final steps of the disclosed process, the product ammonia 23 (still at a high temperature and pressure) is mixed with excess $CO_2$ produced in the carbon black refinery and reacted at a temperature and pressure of about 180° C. and 150 bar, respectively. This stream is intended to be reacted into urea, a common nitrate. For example, if the stream of $NH_3$ and $CO_2$ was used as the feedstock to a nearby urea synthesis plant as disclosed in FIG. 7 below, such a coupling would eliminate or alleviate the need to heat and pressurize the stream before synthesis, and the $CO_2$ formed as a byproduct in the WGS reaction could be saved and fed into the process, both improving urea yield efficacy and preventing the emission of a greenhouse gas.

Figure 4:
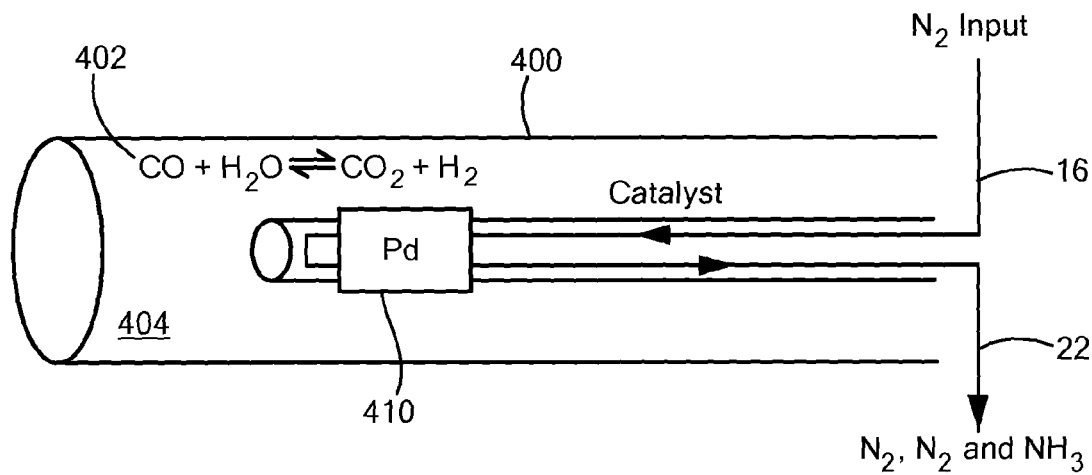
FIG. 4 shows an alternate configuration for coupling thermal demands of the process of FIG. 3.

FIG. 4 shows an alternate configuration for coupling thermal demands of the process of FIG. 3. Referring to FIGS. 3 and 4, and as alluded above with respect to thermocoupling the different steps, the approach of FIG. 4 couples thermal inputs of the carbon monoxide scrubber 204 and the hydrogen separation. FIG. 4 illustrates supporting the ammonia reactor 216 with heat from the hydrogen separator and WGS reactions, specifically by disposing an ammonia reactor within the hydrogen separator environment, thus directing heat from the hydrogen separator to an ammonia reactor for synthesizing the ammonia. Other forms of thermal coupling may be performed, however.

This proposed approach is intended to take place within a pipe 400 or other containment that houses a smaller reactor 410. In this process, a water-gas shift reaction 402 is catalyzed on the outside 404 of the reactor 410, providing heat and hydrogen feedstock for the ammonia synthesis reaction housed within the reactor 410. Nitrogen input 16 is provided externally to combine with $H_2$ resulting from the hydrogen separation, and the resulting $NH_3$ yielded. This combined process, when operated for commercial ammonia production, makes use of an iron catalyst for the WGS reaction and ammonia synthesis reaction, as well as palladium for increased proton transfer.

Figure 5:
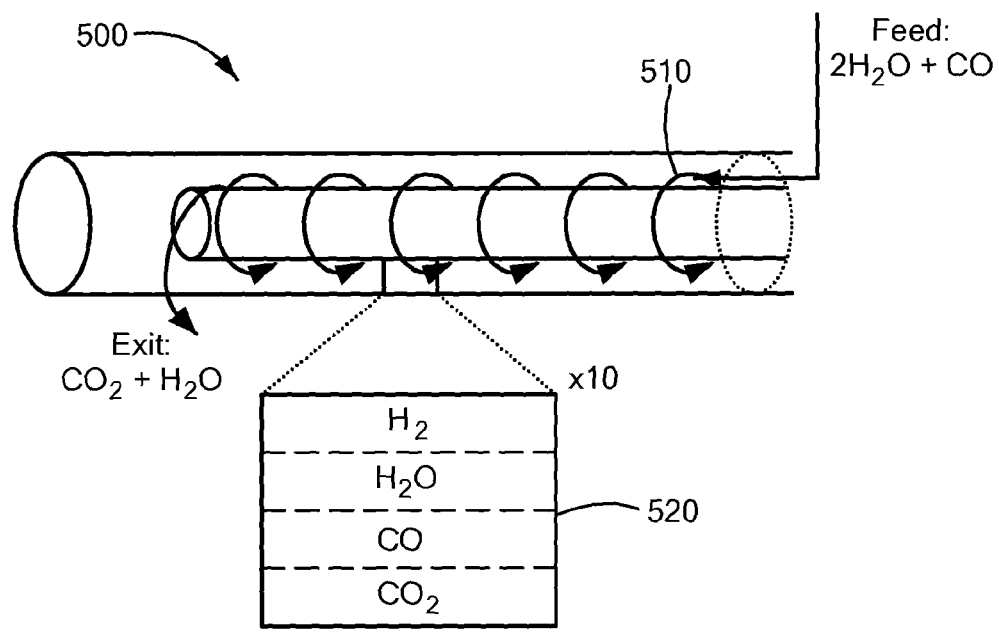
FIG. 5 shows an alternate configuration for a hydrogen separation membrane as in FIG. 3.

FIG. 5 shows an alternate configuration for a hydrogen separation membrane as in FIG. 3. The configuration of FIG. 5 aims to replace the membranes needed in the hydrogen separator with a centrifugal membrane 500. This process is designed to centrifugally separate gases in the membrane. With the use of a palladium-silver membrane 510 for improved hydrogen separation, a centripetal feed forces the gases to separate in order of density, as shown by layering 520, effectively isolating a stream of hydrogen (the lightest molecule present) while forcing heavier molecules through the membrane. This results in a boundary layer of pure hydrogen surrounding the membrane. Such a centrifugal membrane 500 provides better yields than the traditional feedstock of mixed H2 and N2. The flux achieved with a feed of pure hydrogen, separated by a centrifugal membrane, increases hydrogen yield The gases being forced through the membrane are contained in a waste recovery system while the hydrogen stream is fed through a compressor or heat exchanger, then into an ammonia reactor. If developed for commercial use, this centrifugal membrane process could replace the $N_2$ membranes used in current ammonia synthesis, reducing the plant's capital cost while operating at up to 600% efficacy.

Figure 6:
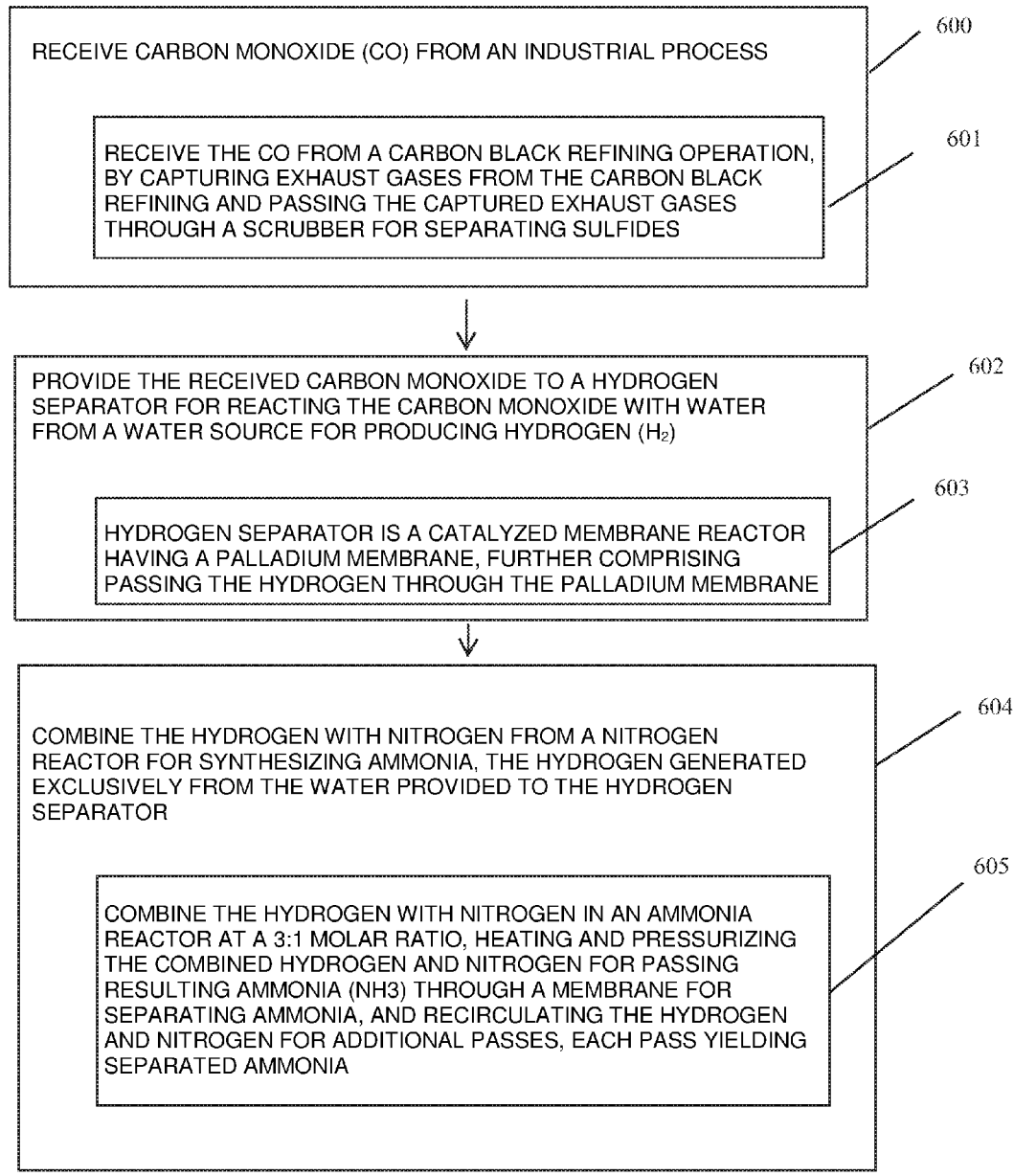
FIG. 6 shows a flowchart of ammonia synthesis as in FIGS. 1-5.

FIG. 6 shows a flowchart of ammonia synthesis as in FIGS. 1-5. Referring to FIGS. 1-6, the method for synthesizing ammonia, as disclosed herein includes, at step 600, receiving carbon monoxide (CO) from an industrial process. In an example configuration, the CO is received from a carbon black refining operation, by capturing exhaust gases from the carbon black refining, and passing the captured exhaust gases through a scrubber 204 or other process for separating sulfides, as depicted at step 601. The disclosed approach strives to utilize and repurpose the byproducts from other industrial processes. This process synthesizes ammonia from exhaust gas leaving a carbon black refinery, using liquid water and atmospheric air as sources for molecular hydrogen and nitrogen, respectively.

Carbon black possesses a range of unique properties that have made it desirable for a variety of applications. Today, the carbon compound is used most commonly as a reinforcing agent in plastic and rubber products, as pigment in paints and inks, and occasionally as automobile and aerospace coating, due to the improved conductivity and UV protection provided by the compound. In the United States, 90% of carbon black is manufactured through an oil furnace process in which a liquid hydrocarbon is heated, continuously pumped into the combustion zone of a natural gas furnace and quickly cooled, ultimately producing carbon black through the incomplete combustion of the feedstock hydrocarbon.20 The exhaust gas from this process contains mostly CO with variable concentrations of sulfides SO2 and H2S, and is fed into a scrubber where the exhaust contaminants are mixed with water and dissolved CO is separated from the mix.

The process provides the received carbon monoxide to a hydrogen separator 210 for reacting the carbon monoxide with water from a water source 212 for producing hydrogen ($H_2$), as disclosed at step 602. The hydrogen separator 210 is a catalyzed membrane reactor having a palladium membrane, which is further operable for passing the hydrogen through the palladium membrane, as depicted at step 603.

From the hydrogen separator 210, the process combines the hydrogen with nitrogen from a nitrogen reactor 214 for synthesizing ammonia, such that the hydrogen is generated exclusively from the water provided to the hydrogen separator 210, in contrast to conventional approaches, which utilize natural gas as the source of hydrogen. In the example arrangement, combining the hydrogen further includes combining the hydrogen with nitrogen in the ammonia reactor 216 at a 3:1 molar ratio, heating and pressurizing the combined hydrogen and nitrogen for passing resulting ammonia ($NH_3$) through a membrane for separating ammonia, and recirculating the hydrogen and nitrogen for additional passes, each pass yielding separated ammonia.

Figure 7:
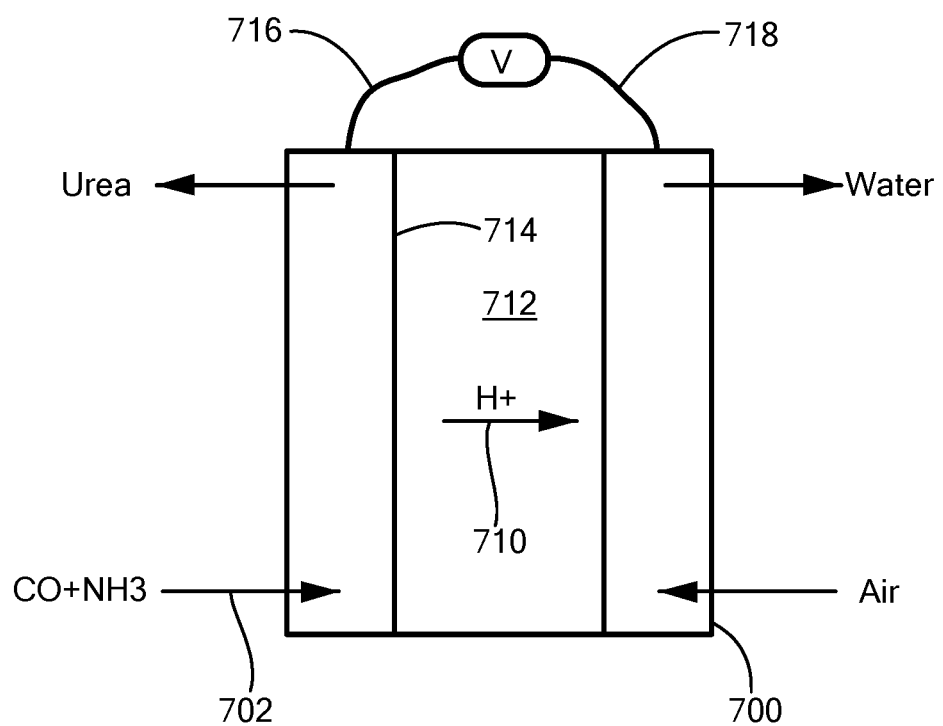
FIG. 7 shows synthesized ammonia of FIG. 5 in a fuel cell for powering the synthesized process.

FIG. 7 shows synthesized ammonia of FIG. 5 in a fuel cell for powering the synthesized process. Referring to FIGS. 5 and 7, a module 700 for a fuel cell is proposed using carbon monoxide CO and ammonia $NH_3$ as fuel 702. The overall reaction is:

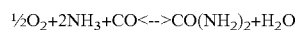

The module 700 depicts production of urea and electricity using a fuel cell; this approach utilizes electro chemistry in the production as shown by the proton transfer of arrow 710. Since urea is a solid with temperatures below 140° C., and considering the product of the fuel cell will be urea in the case of ammonia fuel with carbon monoxide and using a proton exchange module, a Phosphoric Acid Fuel Cell (PAFC) type of chemistry is applicable.

The fuel cell module 700 depicts an electrochemical approach for synthesizing urea from carbon monoxide and ammonia to allow the process to produce electricity as well as urea. The module 700 receives the synthesized ammonia, in which the module has an electrolyte 712, a separator 714, and terminals 716, 718 on opposed sides of the separator. The module 700 converts the received ammonia into urea, such that the conversion results in an ionic flow across the separator 714 for generating a voltage differential between the opposed terminals 716, 718. The generated voltage can be employed elsewhere in the ammonia and/or urea synthesis, such as for operating compressors, pumps or heat exchangers. The electrochemical approach of the synthesis of urea will replace the reactor 820 with a PAFC or a PBI fuel cell such as the module 700. PBIs are pipes membranes that serve the commercial electrochemical synthesis.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A method for synthesizing ammonia, comprising:
receiving carbon monoxide (CO) from a carbon black refining operation, by capturing exhaust gases from the carbon black refining and passing the captured exhaust gases from the carbon black refining and passing the captured exhaust gases through a scrubber for separating sulfides;
providing the received carbon monoxide to a hydrogen separator for reacting the carbon monoxide with water from a water source resulting in hydrogen ($H_2$),
the hydrogen separator further comprising a catalyzed membrane reactor having a palladium membrane;
passing the hydrogen through the palladium membrane;
combining the hydrogen with nitrogen from a nitrogen reactor for synthesizing ammonia, the hydrogen generated exclusively by separation from the water provided to the hydrogen separator, further comprises combining the hydrogen with nitrogen in an ammonia reactor at a 3:1 molar ratio, heating and pressurizing the combined hydrogen and nitrogen and passing resulting ammonia (NH3) through a membrane for separating ammonia, and recirculating the hydrogen and nitrogen for additional passes, each pass yielding separated ammonia.

2. The method of claim 1 wherein the CO is reacted with the water at a molar ratio of 2:1 at a temperature of 450° C., and the hydrogen and nitrogen is combined at 450° C. and at a pressure of 200 bar.

3. The method of claim 1 further comprising reacting the hydrogen and nitrogen in an ammonia reactor using an iron-chromium catalyst.

4. The method of claim 1 further comprising coupling thermal inputs of the carbon monoxide scrubber and the hydrogen separation for facilitating a self-sustaining electrical generation.

5. The method of claim 1 further comprising directing heat from the hydrogen separator to an ammonia reactor for synthesizing the ammonia.

6. The method of claim 1 further comprising:
receiving the synthesized ammonia into a module, the module having an electrolyte, a separator, and terminals on opposed sides of the separator; and
converting the received ammonia into urea, the conversion resulting in an ionic flow across the separator for generating a voltage differential between the opposed terminals.

7. The method of claim 1 further comprising disposing the hydrogen separator and ammonia reactor in proximity to a urea generation process, and coupling the synthesized ammonia and a $CO_2$ stream from the hydrogen separator to the urea generation process, the synthesized ammonia and $CO_2$ stream retaining heat from the ammonia reactor and hydrogen separator, respectively.

8. A method for synthesizing ammonia, comprising:
receiving carbon monoxide (CO) from an industrial process;
providing the received carbon monoxide to a hydrogen separator for reacting the carbon monoxide (CO) with water ($H_2O$) from a water source resulting in hydrogen ($H_2$) and Carbon Dioxide ($CO_2$), the hydrogen formed from the $H_2O$,
the hydrogen separator further comprising a catalyzed membrane reactor having a palladium membrane, further comprising passing the hydrogen through the palladium membrane;
receiving heat via a thermal conduit from an industrial combustion process, the thermal conduit responsive to thermal energy vented as a byproduct from the industrial combustion process for providing heat to the hydrogen separator;
combining the hydrogen with nitrogen from a nitrogen reactor for synthesizing ammonia, further comprising directing heat from the hydrogen separator to an ammonia reactor for synthesizing the ammonia, the hydrogen generated exclusively by separation from the water provided to the hydrogen separator.

9. A method for synthesizing ammonia, comprising:
receiving carbon monoxide (CO) from an industrial process;
providing the received carbon monoxide to a hydrogen separator for reacting the carbon monoxide with water from a water source resulting in hydrogen ($H_2$),
the hydrogen separator further comprising a catalyzed membrane reactor having a palladium membrane, further comprising passing the hydrogen through the palladium membrane;
combining the hydrogen with nitrogen from a nitrogen reactor for synthesizing ammonia, the hydrogen generated exclusively separation from the water provided to the hydrogen separator, further comprising combining the hydrogen with nitrogen in an ammonia reactor at a 3:1 molar ratio, heating and pressurizing the combined hydrogen and nitrogen and passing resulting ammonia ($NH_3$) through a membrane for separating ammonia, and recirculating the hydrogen and nitrogen for additional passes, each pass yielding separated ammonia, further comprising thermally coupling the hydrogen separator and ammonia reactor by disposing the ammonia reactor inside the hydrogen separator.

* * * * *